United States Patent
Yuen (10) Patent No.: US 12,123,526 B2
(45) Date of Patent: Oct. 22, 2024

(54) ASEPTIC CONNECT AND DISCONNECT COUPLER

(71) Applicant: Avantor Fluid Handling LLC, Devens, MA (US)

(72) Inventor: Tat M. Yuen, Lunenburg, MA (US)

(73) Assignee: Avantor Fluid Handling, LLC, Devens, MA (US)

( * ) Notice: Subject to any disclaimer, the term of this patent is extended or adjusted under 35 U.S.C. 154(b) by 0 days.

(21) Appl. No.: 18/238,793

(22) Filed: Aug. 28, 2023

(65) Prior Publication Data
US 2024/0084937 A1   Mar. 14, 2024

Related U.S. Application Data

(60) Provisional application No. 63/405,632, filed on Sep. 12, 2022.

(51) Int. Cl.
*F16L 29/00* (2006.01)

(52) U.S. Cl.
CPC .......... *F16L 29/002* (2013.01); *F16L 29/007* (2013.01); *F16L 2201/44* (2013.01); *Y10T 137/87933* (2015.04)

(58) Field of Classification Search
CPC ..... F16L 37/373; F16L 29/002; F16L 29/007; F16L 2201/44; F16K 11/0853;
(Continued)

(56) References Cited

U.S. PATENT DOCUMENTS 2,333,496 A * 11/1943 Townhill ............. F16L 55/1007
                                                251/309
2,334,875 A * 11/1943 Hufferd ................. F16L 37/373
                                                137/614.01
(Continued)

FOREIGN PATENT DOCUMENTS

DE   102021133085 A1 *  2/2022 ............ F16L 29/002
EP       0961060 A1 * 12/1999

OTHER PUBLICATIONS

Kleenpak Presto Sterile Connector, Pall Biotech, USD3125a; 5 pages 9/18; Kleenpak™ Sterile Connectors (pall.com) https://www.cpcworldwide.com/Biopharma/AseptiQuik# https://www.cpcworldwide.com/Biopharma/AseptiQuik/AseptiQuik-G-DC.
(Continued)

*Primary Examiner* — David Colon-Morales
(74) *Attorney, Agent, or Firm* — Faegre Drinker Biddle & Reath LLP (57) ABSTRACT

A coupler for aseptically coupling and controlling fluid communication between at least two components. The coupler includes a first connector housing with an inner concave surface. A first connector extends from the top of the first connector housing and is adapted to connect to a first component. A first connector conduit extends through the first connector and into the first connector housing so as to define a fluid passageway to an inner opening on the inner surface of the first connector housing. A rotary valve is located within an inner cavity of the first connector housing and includes at least two rotary valve segments. The rotary valve segments are configured to rotate within the cavity. At least one of the rotary valve segments includes a fluid conduit extending through the at least one rotary valve segment.

19 Claims, 9 Drawing Sheets

(58) Field of Classification Search
CPC ..... Y10T 137/87933; A61M 2039/229; A61M 39/223; A61M 39/18; A61M 39/16
See application file for complete search history.

(56) References Cited

U.S. PATENT DOCUMENTS

| | | | | |
|---|---|---|---|---|
| 2,357,232 | A * | 8/1944 | Townhill | F16L 37/373 251/309 |
| 2,373,925 | A * | 4/1945 | Townhill | F16L 29/002 251/309 |
| 2,397,576 | A * | 4/1946 | Townhill | F16L 37/12 137/599.02 |
| 2,399,515 | A * | 4/1946 | Snyder | F16L 37/12 251/367 |
| 2,421,332 | A * | 5/1947 | Johnson | F16L 37/373 251/309 |
| 2,458,899 | A * | 1/1949 | Doubrava | F16L 37/373 251/309 |
| 2,458,910 | A * | 1/1949 | Johnson | F16L 37/12 251/309 |
| 2,663,315 | A * | 12/1953 | Rush | F16L 37/373 285/19 |
| 2,712,454 | A * | 7/1955 | Love | F16K 5/06 251/309 |
| 4,900,322 | A * | 2/1990 | Adams | A61M 39/223 604/410 |
| 4,967,797 | A * | 11/1990 | Manska | A61M 39/223 604/83 |
| 8,215,971 | B2 * | 7/2012 | Bayerbach | H01R 13/64 439/158 |
| 8,360,103 | B2 * | 1/2013 | Pollack | F16K 5/0407 137/614.01 |
| 8,602,058 | B1 | 12/2013 | Del Castillo | |
| 8,746,278 | B2 * | 6/2014 | Py | F16L 37/36 251/340 |
| 9,481,477 | B2 * | 11/2016 | Kjar | C12M 23/40 |
| 9,675,520 | B2 * | 6/2017 | Rogers | B01L 1/02 |
| 2005/0035324 | A1 | 2/2005 | McPeak et al. | |
| 2011/0240158 | A1 | 10/2011 | Py | |
| 2013/0292592 | A1 | 11/2013 | Py | |
| 2017/0340874 | A1 | 11/2017 | Gerst et al. | |
| 2018/0117298 | A1 | 5/2018 | Tessarin | |
| 2021/0095802 | A1 | 4/2021 | Andrews et al. | |
| 2021/0199220 | A1 | 7/2021 | Truong | |
| 2022/0074531 | A1 * | 3/2022 | Rowen | F16L 37/252 |

OTHER PUBLICATIONS

Genderless Sterile Connection Technology—A Quality By Design (QbD) Approach for Greater Sterility Assurance from Manufacturing To Use; Pall Biotech, USD3164b; 15 pages, 10/20; https://shop.pall.com/US/en/products/sterile-connectors/kleenpak-presto-sterile-connectors.

Extended European Search Report for Corresponding EP Application No. 23194622.9 dated Feb. 7, 2024, 10 pages.

* cited by examiner

ASEPTIC CONNECT AND DISCONNECT COUPLER

RELATED APPLICATION

This application is related to and claims priority from U.S. Provisional Application 63/405,632, filed on Sep. 12, 2022, the disclosure of which is incorporated herein by reference in its entirety.

TECHNICAL FIELD

The invention relates to fluid coupling devices for fluid systems and, more particularly, to a rotary coupling device for aseptically connecting and disconnecting fluid lines.

BACKGROUND INFORMATION

In some fluid systems, such as some bioprocessing fluid systems or blood handling systems, it may be desirable, or in some cases necessary, to includes a coupler that can aseptically connect and disconnect sterilized fluid lines, containers or equipment while maintaining sterility. For example, it may be desirable to aseptically connect and disconnect one or more fluid media bags or containers from a fluid line. In order to do so, an aseptic coupling is typically used to connect the fluid line or outlet on the fluid media container, while substantially inhibiting biological contamination of the fluid media container and the fluid line. Similarly, it may be desirable to couple a fluid pathway from a piece of processing equipment to another fluid pathway from a secondary piece of processing equipment container while maintaining a sterile pathway for fluid flow.

Many types of aseptic coupling exist that include two coupling portions that can be attached and detached from one another. However, most such couplies are fairly complex or result in excessive fluid existing between the two disconnected coupling portions which can result in inadvertent exposure to the surrounding environment. In order to minimize any such fluid, it is typically necessary to add a clamping device upstream of the aseptic coupling to close off the flow through the aseptic coupling before separation.

A need exists for an improved aseptic coupling system.

SUMMARY OF THE EMBODIMENTS

A coupler for aseptically coupling and controlling fluid communication between at least two components is disclosed. The coupler includes a first connector housing including two opposed side walls, two opposed end walls, a top section and an open bottom. The side walls, the end walls and the top section each having respective inner surfaces that, in combination, define an inner cavity. The inner surfaces of the top section and the side sections define, in combination, a concave surface that has a shape that defines a portion of a cylinder.

A first connector is formed on or attached to and extends from the top section. The first connector is adapted to connect to a first component of the at least two components.

A first connector conduit extends through the first connector and the top section of the first connector housing so as to define a fluid passageway from an outer opening at an upper end of the first connector to an inner opening on the inner surface of the top section of the first connector housing.

A rotary valve is located within the inner cavity of the first connector housing and has a longitudinal axis. The rotary valve includes at least two rotary valve segments. Each rotary valve segment includes a valve segment outer surface and a valve segment inner surface. The valve segment outer surface has a curved surface that defines a portion of cylinder. The valve segment inner surface has at least one inner planar surface. The valve segment inner surface of one of the rotary valve segments is configured to contact the valve inner surface of an adjacent rotary valve segment. The curved outer surfaces of the rotary valve segments, in combination, define a cylindrical surface. The rotary valve segments are configured to rotate about the longitudinal axis within the cavity and against the concave inner surface of the first connector housing.

At least one of the at least two rotary valve segments includes a fluid conduit extending through the at least one rotary valve segment from a first opening to a second opening. The first opening is positioned so that:

in a first rotational position of the at least one rotary valve segment relative to the first connector housing corresponding to the open state, the first opening aligns with the inner opening of the first connector conduit in the connector housing, and the second opening of the fluid conduit simultaneously aligns with an inner opening on a second connector conduit so as to provide a fluid path from the outer opening of the first connector conduit and into the second connector conduit, and in a second rotational position of the at least one rotary valve segment relative to the first connector housing corresponding to the closed state, the first opening does not align with the inner opening of the first connector conduit in the connector housing, the second opening of the fluid conduit does not align with the inner opening on the second connector conduit, and the valve segment outer surface of one of the at least two rotary valve segments blocks the inner opening of the first connector housing and the valve segment outer surface of the other of the at least two rotary valve segments blocks the inner opening of the second connector housing such that no fluid path is provided from the first connector conduit to the second connector conduit through either of the at least two rotary valve segments.

In an embodiment, the coupler includes a second connector housing adjacent to the first connect housing. The second connector housing has a second connector extending outward from a surface on the second connector housing. The second connector conduit extends through the second connector housing and the second connector. The second connector is adapted to connect to a second component of the at least two components to thereby provide a fluid flow path between the first component and the second component.

In an embodiment, the second connector is a cap for a container and the second component is a container configured to store a fluid.

In an embodiment, the second connector housing is a manifold which is configured to receive multiple first connector housings.

In one embodiment, the second connector housing includes two opposed side walls, two opposed end walls, a top section and an open bottom. The side walls, the end walls and the top section each have respective inner surfaces that, in combination, define an inner cavity. The inner surfaces of the top section and the side sections define, in combination, a concave surface that has a shape that defines a portion of a cylinder. When the first and second connector housings are adjacent to one another the combination of the concave surfaces of the first and second connector housings form a substantially cylindrical shape.

Preferably when the coupler is in the closed state, the first connector housing can be aseptically separated from the second connector housing so that the inner openings of the first and second connector conduits are not exposed to an ambient environment.

When the coupler is in the closed state, preferably at least one rotary valve segment is attached to the first connector housing such that the rotary valve segment cannot be readily removed from the first connector housing except by rotating the rotary valve segment relative to the first connector housing.

Each end wall of the first connector housing may include a protrusion extending into the cavity at a location radially inward from the side wall. Each protrusion is configured to mate with a corresponding recess formed in a longitudinal end of the corresponding rotary valve segment.

In one arrangement, there are three rotary valve segments and three connectors. Two of the rotary valve segments include fluid conduits and the third rotary valve segment does not include any fluid conduit.

In one configuration, there are two connectors extending from the top of the first connector housing.

The connectors may be hose barb connectors, each configured to connect with a separate hose that is coupled to an associated component.

The second connector may be a cap with threads that engage with the neck of a container.

In one embodiment, the coupler includes at least three connector housings and the rotary valve includes at least three rotary valve segments.

In another embodiment, the coupler includes two rotary valve segments and the valve segment outer surface of each rotary valve segment defines a semicylindrical surface. The valve segment inner surface of each rotary valve segment is a planar surface.

The coupler may include a second connector housing adjacent to the first connect housing. The second connector housing has a second connector extending outward from a surface on the second connector housing. The second connector conduit extends through the second connector housing and the second connector. The second connector is adapted to connect to a second component of the at least two components to thereby provide a fluid flow path between the first component and the second component.

Preferably each rotary valve segment includes a tab that is attached to or formed integral with a longitudinal end of the rotary valve segment.

The tab may include a neck portion which is smaller in cross-section than the rotary valve segment. The neck portion seats within a first notch in one of the end walls. The first notch provides support for and permits rotation of the neck portion relative to the first connector housing.

Each rotary valve segment may include a protrusion that extends axially out of a longitudinal end of the rotary valve segment on an opposite side from the tab. The protrusion seats within a second notch in the other end wall of the connector housing. The second notch provides support for and permits rotation of the protrusion relative to the connector housing.

The coupler may include an assembly enclosure with two side walls that are spaced apart from one another a sufficient distance to receive the first and second connector housings. The assembly enclosure has top and bottom walls that are also spaced apart a distance too receive the first and second connector housings therebetween. The top and bottom walls each include a notch to permit the first and second connectors to extend out of the assembly enclosure. The assembly enclosure has a back wall with a hole formed through it with notches on opposed sides that are sized and positioned so to permit the tabs on the at least two rotary valve segments to pass through and extend out of the enclosure when the closure is in its closed state. The hole is sized to receive the neck portions of the tabs and permit the neck portions to rotate freely relative to the enclosure. When the closure is in its closed state, the notches and hole permit the enclosure to be slid on and off the first and second connector housings. When the closure is in its open position, the tabs are rotated relative to the notches so that the tabs prevent removal of the assembly enclosure.

The foregoing and other features of the invention and advantages of the present invention will become more apparent in light of the following detailed description of the preferred embodiments, as illustrated in the accompanying figures. As will be realized, the invention is capable of modifications in various respects, all without departing from the invention. Accordingly, the drawings and the description are to be regarded as illustrative in nature, and not as restrictive.

BRIEF DESCRIPTION OF THE DRAWINGS

For the purpose of the illustrating the invention, the drawings show a form of the invention which is presently preferred. However, it should be understood that this invention is not limited to the precise arrangements and instrumentalities shown in the drawings.

DESCRIPTION OF THE EMBODIMENTS

Referring to the drawings, wherein like reference numerals illustrate corresponding or similar elements throughout the several views, FIGS. 1 to 4 illustrate an embodiment of an aseptic coupler 10 according to the present invention. The coupler 10 includes at least one connector housing 12. Preferably, there are at least a first connector housing and a second connector housing. Each connector housing 12 includes two opposed side walls 12A, end walls 12B, a top section 12C and an open bottom. The inner surfaces of the side walls, end walls and top section define an inner cavity 14.

Each connector housing 12 is configured to engage, connect, attach, or be mounted to a component, at least one component of which it is desired to maintain sterility and/or reduce or minimize contamination from external or environmental sources. In many cases it is desirable to prevent contamination of all components attached to the coupler 10. The present invention is applicable in either case. The component may be a fluid media bag or container, for example a biofluid, chemical or medical fluid container, or processing equipment, for example, a bioreactor or biofluid pump, or to tubing connecting to any of the foregoing.

In the illustrated embodiment, each connector housing 12 includes at least one connector 16 that is formed on or attached to and extends from the top section 12 and provides a fluid pathway into the associated connector housing. In the illustrated embodiment, there are two connectors 16 shown that are hose barb connectors, each configured to connect with a separate hose that is coupled to an associated component. However, it should be understood that the connector 16 could, instead, be a cap with threads that engage with the neck of a container. See FIGS. 2A and 2B. Other attachment mechanisms that are used in the field may be substituted for the barbed connectors. In the illustrated embodiment, the connector 16 is shown as an integral extension of the connector housing 12. However, it is also contemplated that the connector 16 could be a separate component that is attached to the connector housing 12. While two barbs 16 are shown on each connector housing 12 the present invention may be used with a single connector 16 or many other variations.

Figure 1:
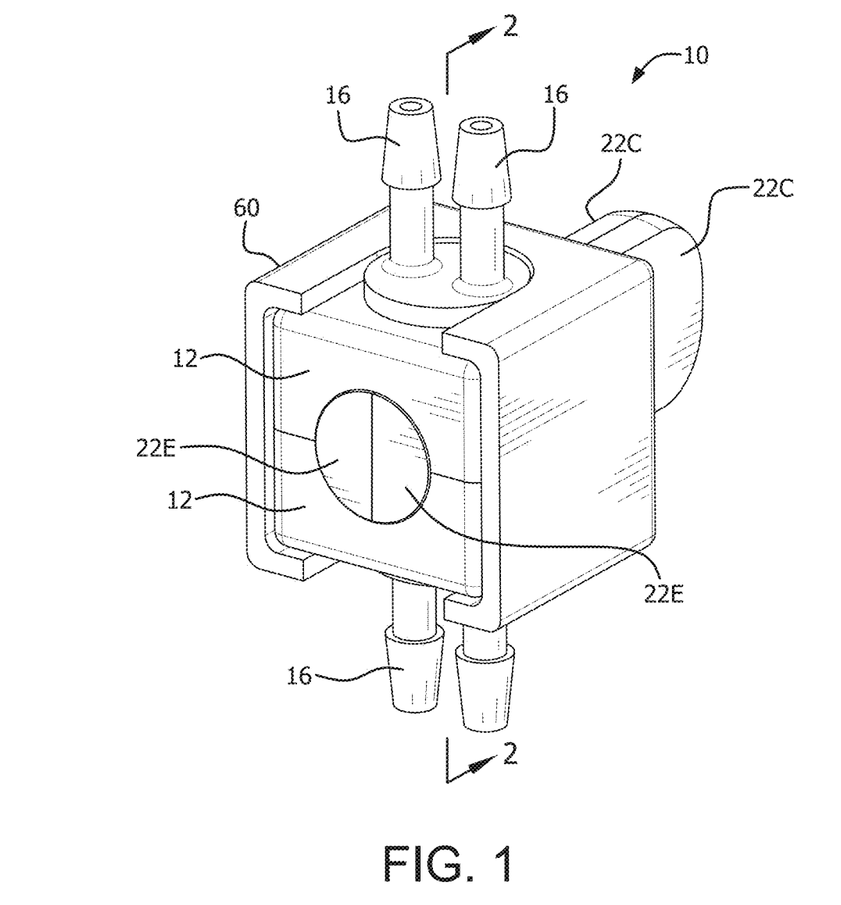
FIG. 1 is a perspective view of an embodiment of an aseptic coupler according to the present invention illustrating the coupler in its open state.
Figure 2:
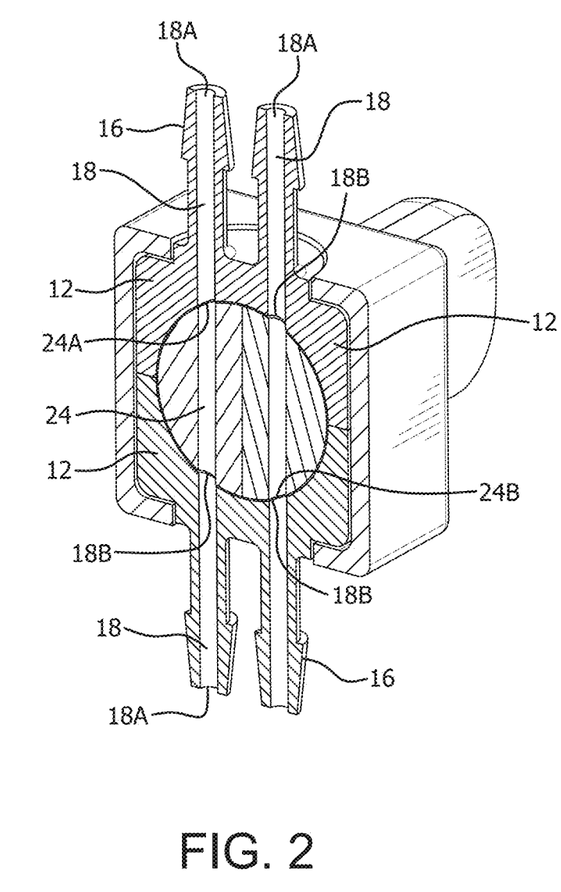
FIG. 2 is a cross-sectional view of the aseptic coupler taken along lines FIG. 2-2 in FIG. 1.
Figure 2A:
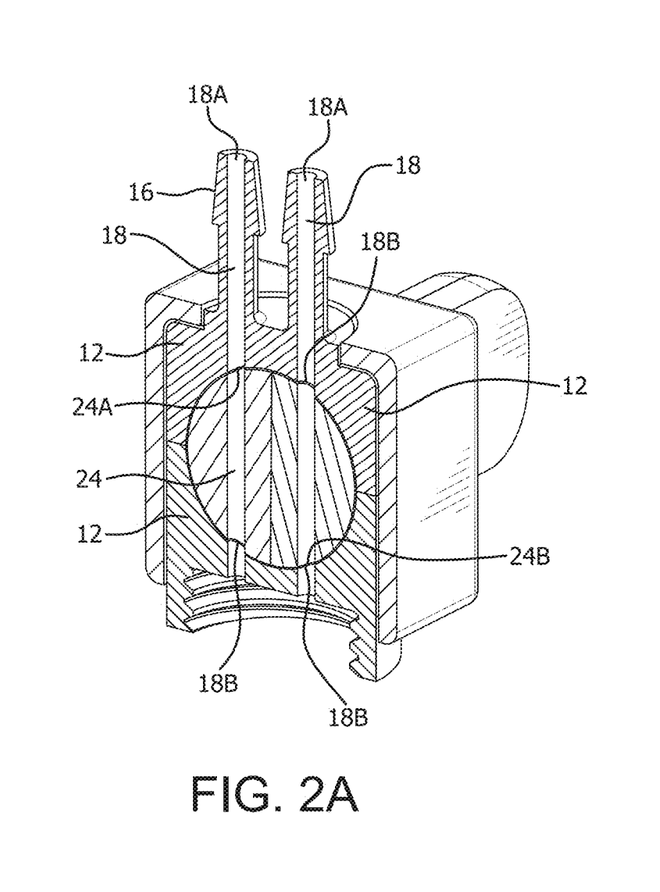
FIG. 2A is a cross-sectional view of an alternate embodiment of the aseptic coupler with a cap as a second connector.
Figure 2B:
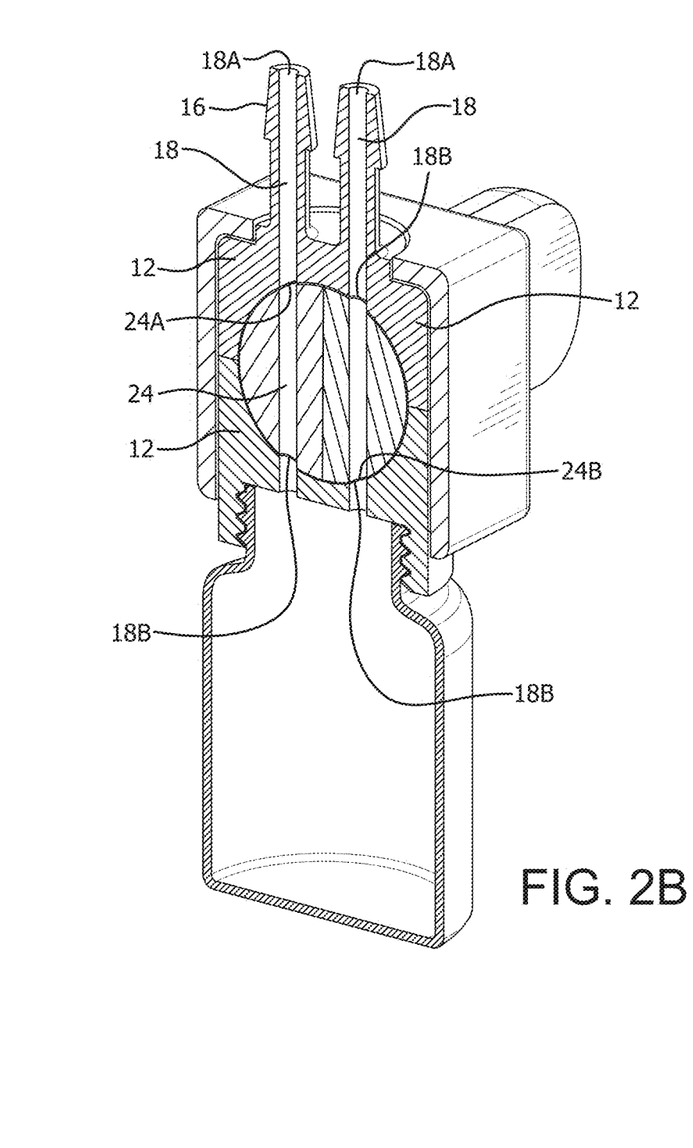
FIG. 2B is a cross-sectional view of the aseptic coupler of FIG. 2A illustrating the second connector attached to a container in cross-section.
Figures 3, 4:
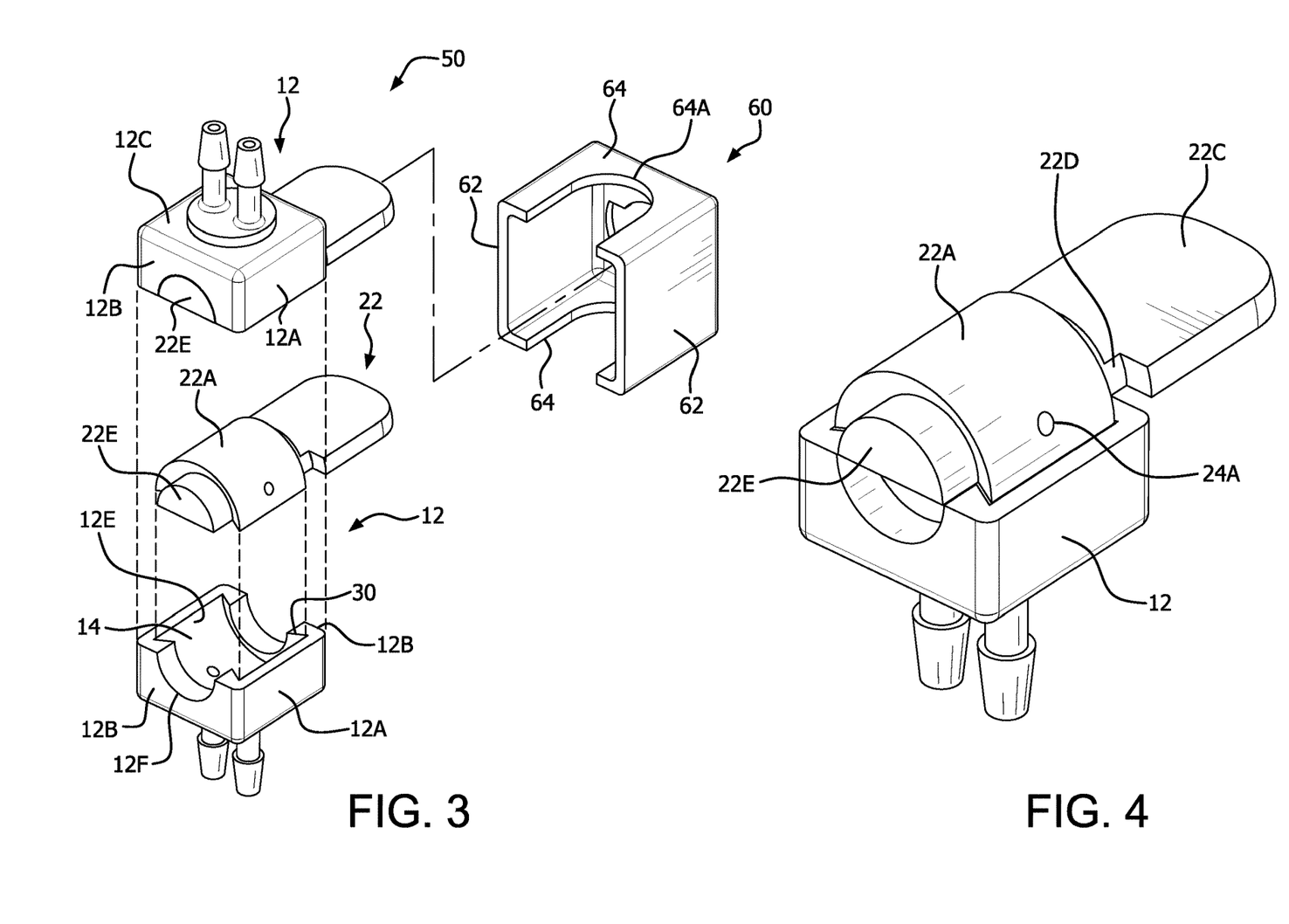
FIG. 3 is a partial exploded view of the aseptic coupler of FIG. 1.
FIG. 4 is a perspective view of a connector housing and rotary valve segment prior to assembly.
Figure 5:
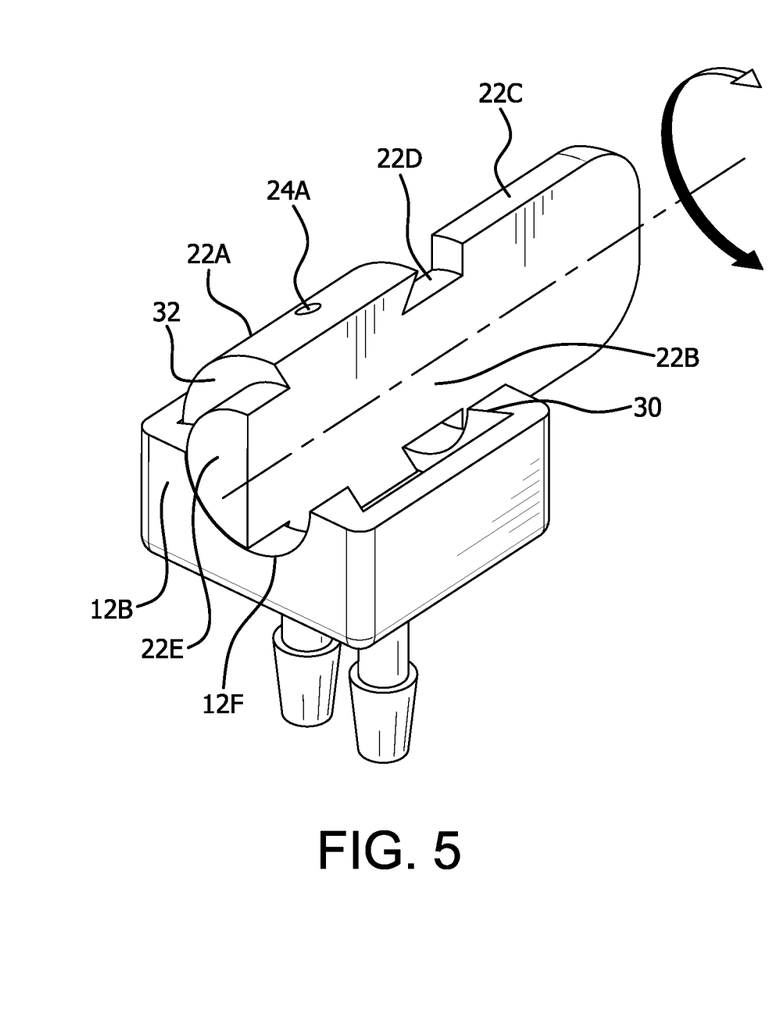
FIG. 5 is a perspective view of the connector housing and rotary valve segment of FIG. 4 as the rotary valve segment is being rotated.

Referring to FIG. 2, the connector 16 and connector housing 12 include a connector conduit 18 that extends from an outer opening 18A in the upper end of the connector 16 to an inner opening 18B on the inner surface of the top section 12C of the connector housing 12. The connector conduit 18 provides a fluid passageway between the outer opening 18A of the connector 16 and the inner cavity 14.

In order to control flow between the fluid passage 18 in one connector housing 12 to the fluid passage 18 in the other connector housing 12, the present invention includes a rotary valve 20. More specifically and with reference to FIGS. 3-6, the rotary valve 20 is located between the inner cavities 14 of the connector housings 12. In the illustrated embodiment, the rotary valve 20 includes two rotary valve segments 22, which each define half of the rotary valve. It should be apparent that if the coupler were configured with three or more connection housings, the rotary valve 20 would have an equal number of rotary valve segments 22.

Each rotary valve segment 22 includes a semi-cylindrical valve portion 22A and an inner surface 22B. Since there are two rotary valve segments 22 in the illustrated embodiment, the inner surface 22B is substantially flat such that when the two segments 22 are placed together, the flat surfaces 22B lie against one another.

Each rotary valve segment 22 is configured to rotatably mount within a corresponding connector housing 12. In order to provide for the desired rotation, the inner surfaces of the side walls and the top section preferably define a semi-cylindrical recess 12E in the interior of the connector housing 12 that is complementary to the outer portion 22A of the rotary valve segment 22 such that when a rotary valve segment 22 is rotated about its longitudinal axis LA, the outer portion 22A rotates along the surface of the recess 12E.

In an embodiment, each rotary valve segment 22 includes a tab 22C that is preferably attached to or formed integral with the semi-cylindrical valve outer portion 22A and/or the inner surface 22B. The tab 22C preferably includes a neck portion 22D which is narrower than the remainder of the rotary valve segment 22. As shown in the figures, when the rotary valve segment 22 is attached to the connector housing 12, the neck portion 22D is preferably semi-cylindrical in shape and seats within a notch 12F in one of the end walls 12B. The rotary valve segment 22 may include a semi-cylindrical protrusion 22E extending axially out of the end of the rotary valve segment 22 on the opposite from the tab 22C. Similar to the neck portion 12D, the protrusion 22E seats within a notch 12F in the other end wall 12B of the connector housing 12. The notches 12F provide rotational support for the rotary valve segment 22.

At least one rotary valve segment 22 includes a fluid conduit 24 extending through the rotary valve segment 22 from a first opening 24A to a second opening 24B. As will be discussed in more detail below, the first opening 24A is positioned within the rotary valve segment 22 so that it aligns with the inner opening 18B of the connector conduit 18 one of the connector housings 12 in a certain rotary position of the rotary valve segment 22. The second opening 24B simultaneously aligns with either the inner opening 18B of the connector conduit 18 of another connector housing 12 (or to fluid conduit 24 in another rotary valve segment 22). Accordingly, when a fluid conduit 24 is aligned with one or more connector conduits 18, i.e., the open state of the coupler 10, a continuous aseptic flow path is created from the connector in one connector housing to the connector housing in another connector housing. Similarly, when the fluid conduit 24 is not aligned with one or more connector conduits 18, i.e., the closed state of the coupler 10, a flow path does not exist from the connector in one connector housing through the rotary valve 20 and, instead a seal is formed at the inner opening 18B, thus preventing flow into the cavity 14. The use of a rotary valve 20 in the present invention allows for a tight fluid seal between the rotary valve segment 22 and the connector housing 12 so as to minimize fluid escaping and environmental infiltration.

One of the benefits of using segments 22 as part of the rotary valve 20 is that when the coupler 10 is in its closed state, the segments 22 can be configured to permit the connector housings 12 to be separated from one another while still maintaining an aseptic seal. More specifically, the rotary valve segments 22 are preferably mounted to the connector housing 12 such that while the rotary valve segment 22 is attached to a connector housing 12, they can be rotated relative to the connector housing 12, but cannot be removed from the connector housing 12. In the illustrated embodiment, the attachment of the rotary valve segment to the connector housing is through a locking connection that inhibits lateral movement. For example, in the illustrate embodiment, each end wall 12B includes a protrusion 30 extending into the cavity 14 at a location radially inward from the side wall 12A. The protrusion 30 mates with a corresponding recess 32 formed in the semi-cylindrical valve portion 22A. In the illustrated embodiment, the locking connection is a dovetail connection with the protrusion 30 having a dovetail shape (e.g., wedge) that curves around the notches 12F in each end wall 12B. The recesses 32 in the valve portions 22A include a complementary curved dovetail shape. As such, when the rotary valve segment 22 is attached to the connector housing 12, such as shown in FIG. 6, it is not possible to separate the rotary valve segment from the connector housing except by rotating the segment 22 out of engagement.

Figure 6:
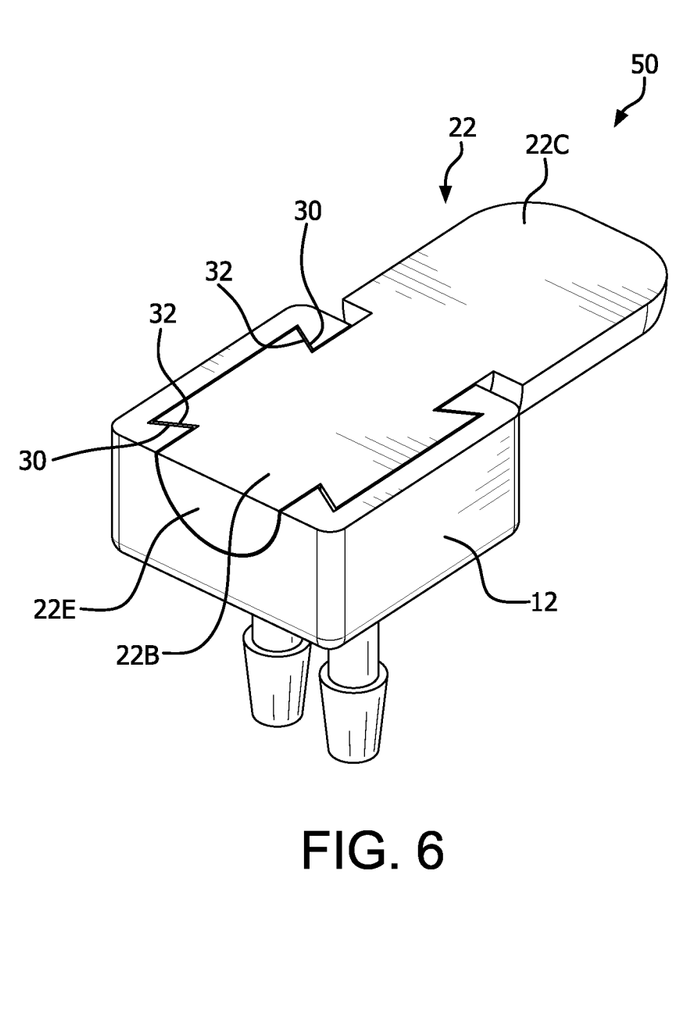
FIG. 6 is a perspective view of the connector housing and rotary valve segment of FIG. 4 with the rotary valve segment as a completed valve assembly with the valve assembly in its closed state.

In order to assemble the closure 10 prior to use, each rotary valve segment 22 must first be engaged to a corresponding connector housing 12 which is depicted in FIGS. 3-6. The rotary valve segment 22 is placed on top of the connector housing 12 with the semi-cylindrical valve portion 22A facing away from the cavity 14 of the connector housing 12 (i.e., the inner surface 22B facing the cavity 14). The rotary valve segment 22 is rotated by grasping the tab 22C and turning so that the protrusions 30 on the end walls 12B extend into the recesses 32 in the semi-cylindrical valve portion 22A while the neck portion 22. As the rotary valve segment 22 is rotated, its inner surface 22B rotates upward until the valve assembly is as shown in FIG. 6 (the closed state of the closure.)

Once each rotary valve segment and connector housing is assembled and in the closed state, and the valve assembly 50 is, preferably, sterilized, the desired components are attached to the applicable connector 16. At this point no fluid can flow through the connector 16 since the semi-cylindrical valve portion 22A is blocking the inner opening 18B of the connector conduit 18. A second valve assembly 50 is inverted and placed on top of the first valve assembly 50. It is possible now to lock the two valve assemblies together by turning both tabs simultaneously so that the rotary valve segment 22 of one valve assembly 50 begins to engage with the connector housing 12 on the other valve assembly (i.e., the recesses 32 on the rotary valve segment 22 of one valve assembly rotate into mating engagement with the protrusions 30 on the connector housing 12 of the other valve assembly 50.) Once the mating starts, the two assemblies 50 are locked into engagement with one another.

When the rotary valve segments 22 are rotated 90 degrees from the closed state, the coupler 10 will be in its open state and the connector(s) 16 on one connector housing 12 will be in fluid communication with the connector(s) on the other connector housing. This is depicted in the cross-section of FIG. 2.

If it is desired to provide additional protection against inadvertent separation of the valve assemblies 50, an assembly enclosure 60 may be used. In the embodiment illustrated in FIGS. 3 and 7, the assembly enclosure 60 includes two side walls 62 that are spaced apart a sufficient distance to receive the valve assemblies 50. The assembly enclosure 60 has top and bottom walls 64 that are also spaced apart a distance too receive the valve assemblies 50 and includes notches 64A to permit the connectors 16 to extend out of the enclosure 60 (see, FIG. 1.)

Figure 7:
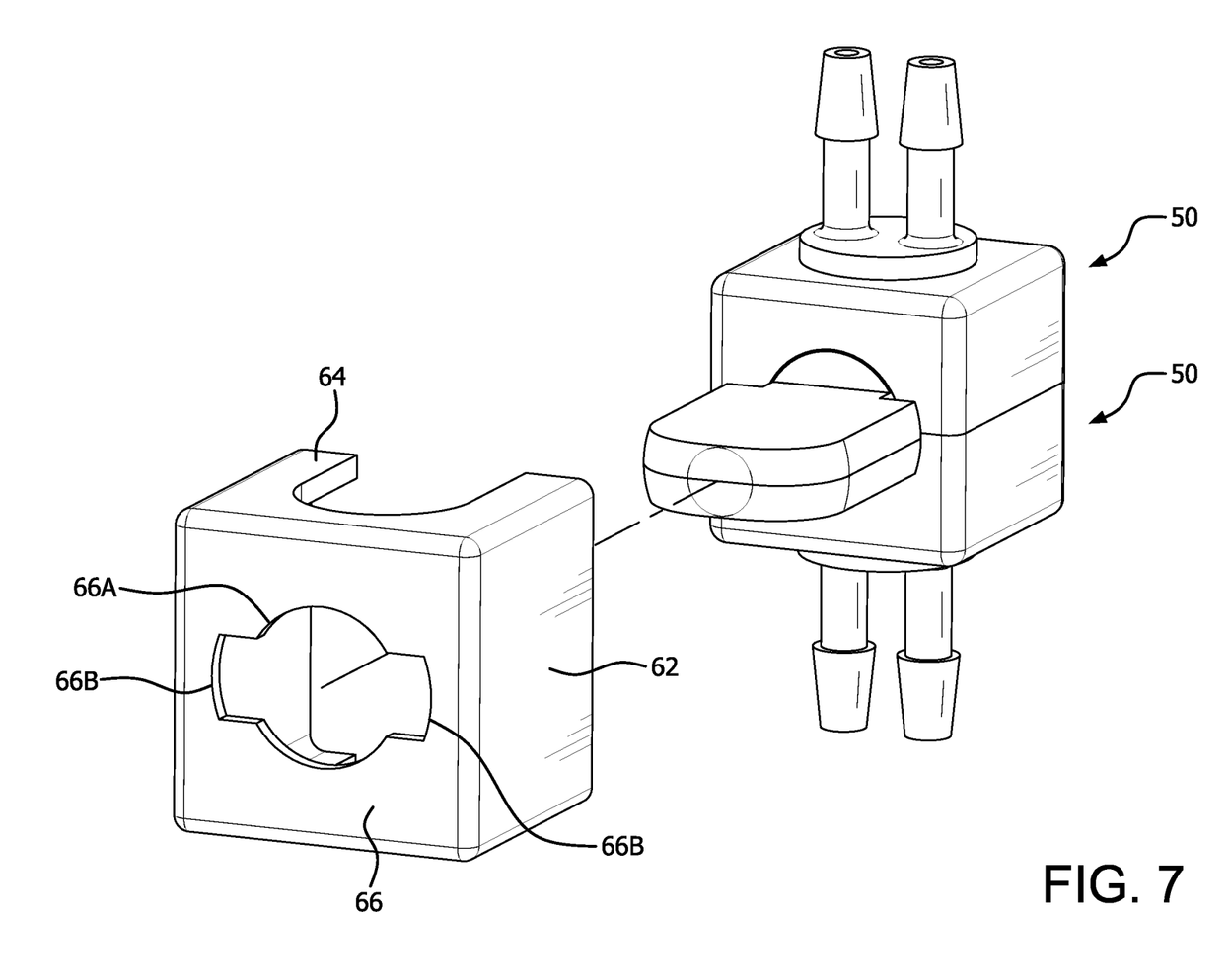
FIG. 7 is a perspective view of an enclosure prior to attachment to two valve assemblies.
Figure 8:
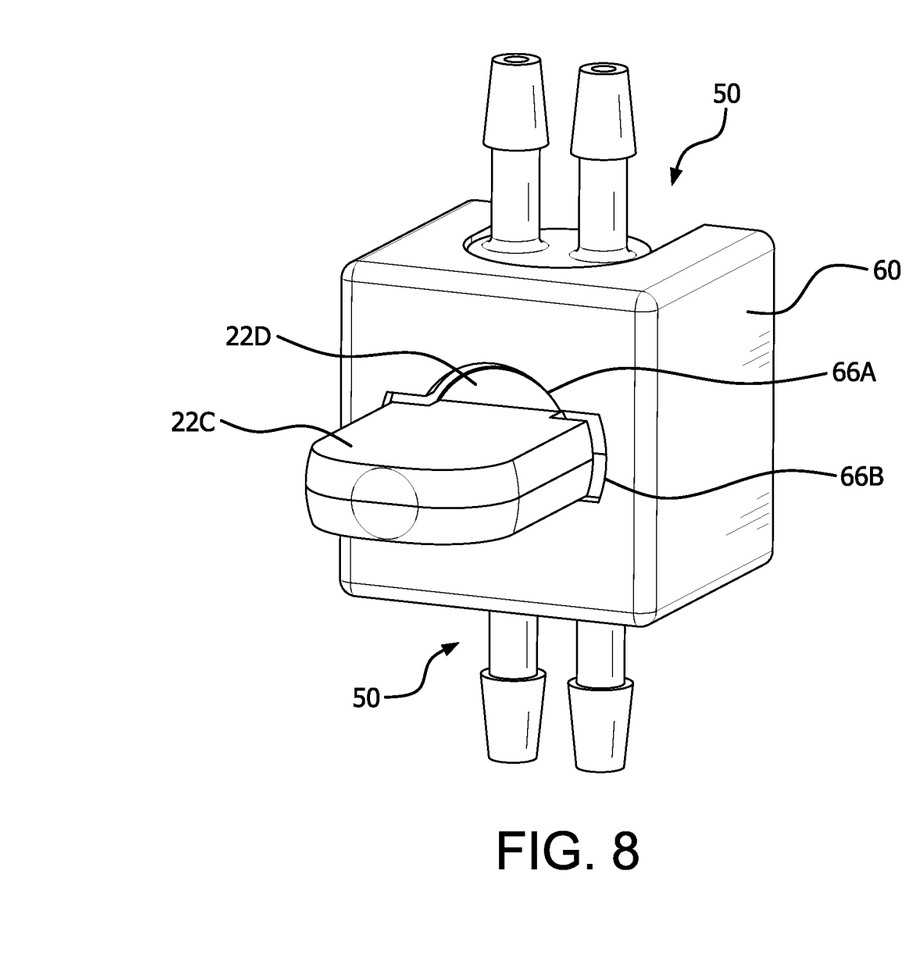
FIG. 8 is a perspective view showing the enclosure attached to the valve assemblies with the valve assemblies in the closed state.
Figure 9:
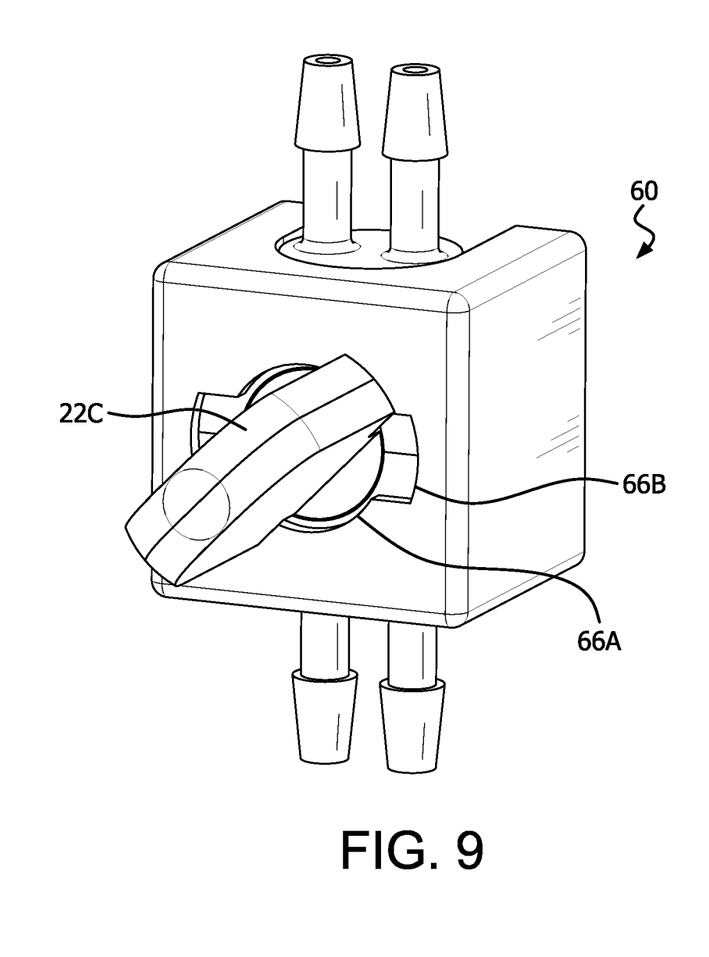
FIG. 9 is a perspective view showing the enclosure attached to the valve assemblies with the tabs turning the rotary valve segments from closed state to the open state.
Figure 10:
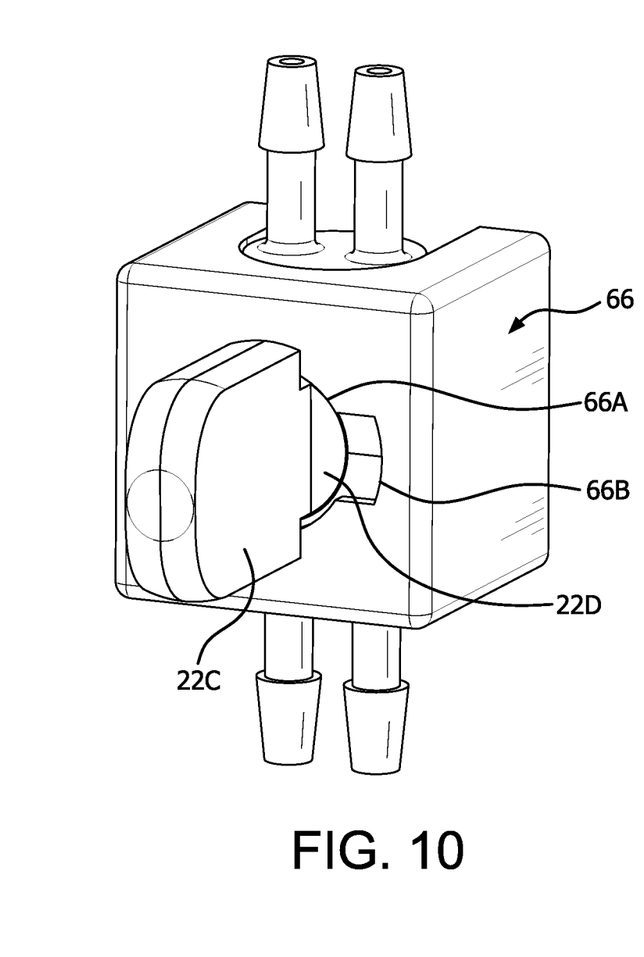
FIG. 10 is a perspective view showing the enclosure attached to the valve assemblies with the tabs rotated so that the valve assemblies are in the open state.

The enclosure also includes a back wall 66 that has a hole 66A formed through it with notches 66B on opposed sides that are sized and positioned so to permit the tabs 22C to pass through and extend out of the enclosure 60 (see, FIG. 8) only when the valve assembles 50 are in their closed state. The hole 66A is sized to allow the neck portion 22D to rotate freely relative to the enclosure 60. As shown in FIGS. 7 and 8, when the valve assemblies 50 are in their closed state, the notches 66B and hole 66A permit the enclosure 60 to be slid over the two valve assemblies 50. As the tabs 22C are rotated, the valve assemblies 50 can no longer be removed from the enclosure 60. This prevents inadvertent separation of the valve assemblies 50 except in the closed state.

Figure 11:
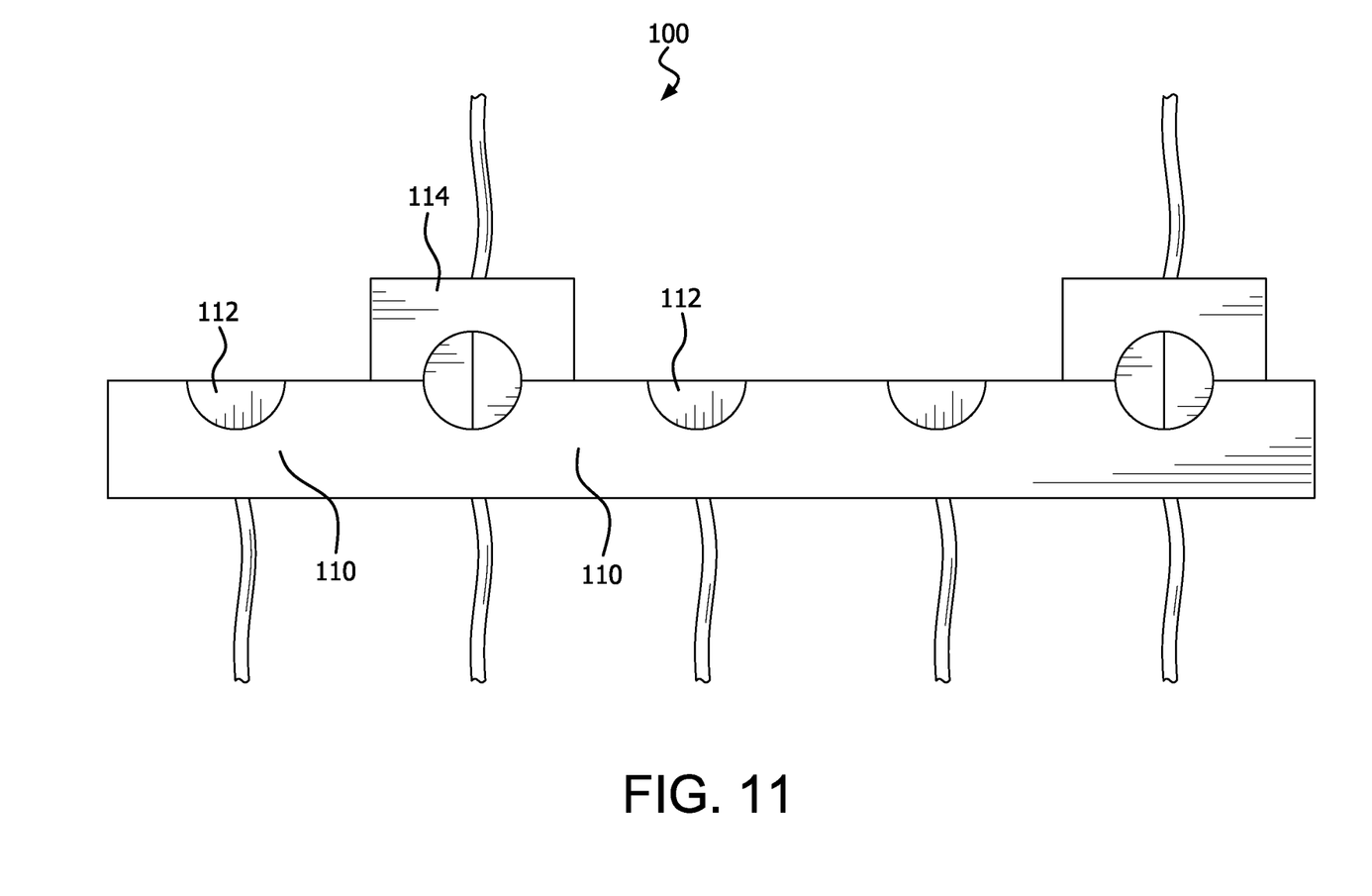
FIG. 11 is a schematic view of an embodiment of the present invention where multiple valve assemblies are attached to a manifold assembly.

Referring to FIG. 11, it is also contemplated that the present invention could be part of a manifold assembly 100. For example, multiple connector housings 110 could be attached or formed integrally side-by-side, each with its own rotary valve segment 112 to form multiple valve assemblies aligned in parallel as part of a lower manifold. Each would provide an aseptic connection to a component. Individual second valve assemblies 114 would then be attached on the top as described above with respect to the particular component that the user needs to connect to aseptically.

Figure 12A:
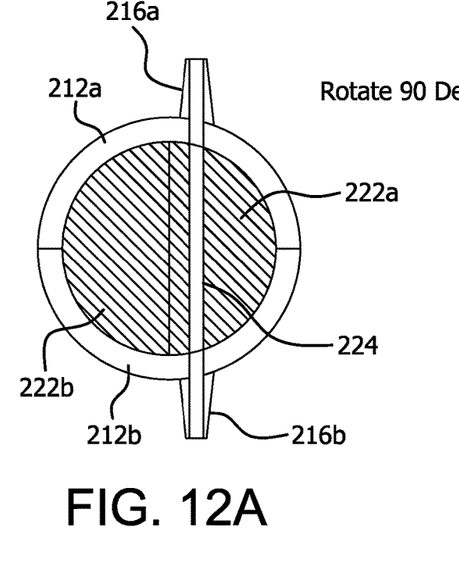
FIGS. 12A and 12B schematically depict an embodiment of the closure with two rotary valve segments with a fluid conduit extending through only one rotary valve segment.
Figure 12B:
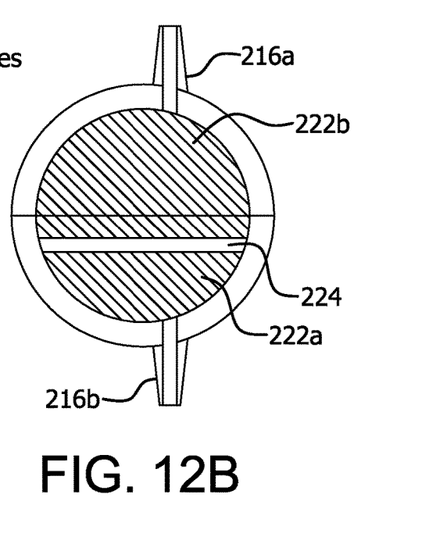

Referring to FIGS. 12A and 12B, an embodiment of the invention is shown which includes two rotary valve segments 222a, 222b, two connector housings 212a, 212b, one first connector 216a and one second connector 216b. All the features described above are part of this embodiment, but not shown and described for the sake of simplicity. In this configuration, only one of the rotary valve segments 222a includes a fluid conduit 224. Referring to FIG. 12A, in the rotational orientation shown, the fluid conduit 224 in the first rotary valve segment aligns with connector conduit in the first connector 216a and the connector conduit in the second connector 216b. Upon rotation of the tabs (not shown) so that the rotary segments are in the orientation shown in FIG. 12B, which corresponds to the closed state, the fluid conduit 224 is not aligned with the connector conduits and the inner openings in the connector conduits are aseptically sealed. Thus, the top connector housing 212a and rotary valve segment 222b can be separated from the bottom connector housing 212b and the rotary valve segment 222a.

Figure 13A:
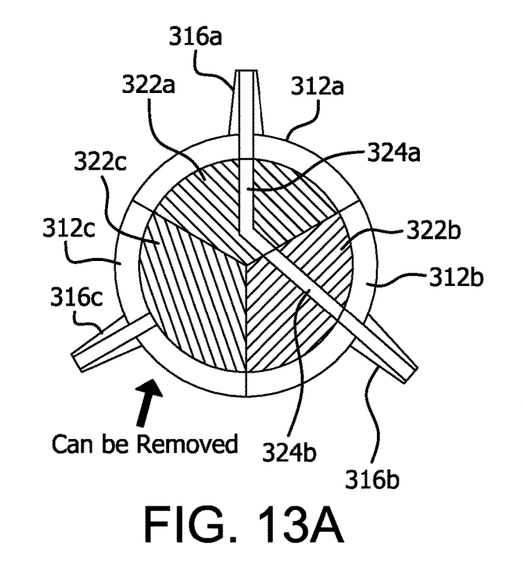
FIGS. 13A and 13B schematically depict an embodiment of the closure with three rotary valve segments with a fluid conduit extending through only two rotary valve segments so that one of the rotary valve segments can be aseptically removed.
Figure 13B:
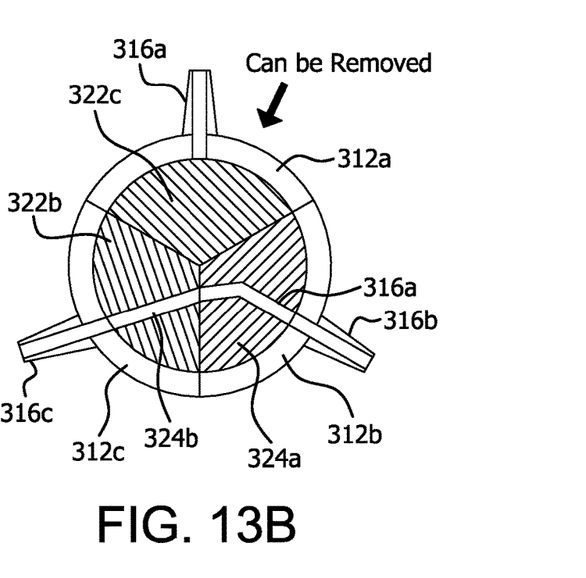

Referring to FIGS. 13A and 13B, another embodiment of the invention is shown. All the features described above are part of this embodiment, but not shown and described for the sake of simplicity. In this configuration, there are three rotary valve segments 322a, 322b, 322c, three connector housings 312a, 312b, 312c, a first connector 316a, a second connector 316b and a third connector 316c. In this embodiment, two of the rotary valve segments 322a, 322b include fluid conduits 324a, 324b. The fluid conduits 324a, 324b are arranged so that that are aligned with one another so as to provide a fluid path between the two rotary valve segments 322a, 322b. The third rotary valve segment 322c does not include a fluid conduit. Referring to FIG. 13A, in the rotational orientation shown, the fluid conduit 324a in the first rotary valve segment aligns with connector conduit in the first connector 316a and the fluid conduit 324b in the second rotary valve segment 322b. The fluid conduit 324b in the second rotary valve segment is aligned with the connector conduit in the second connector 316b. The third connector 316c is aseptically sealed off from the other rotary valve segments 322a, 322b by the third rotary segment 322c. Thus, third connector housing 312c and its rotary valve segment 322c can be safely removed.

Upon rotation of the tabs (not shown) so that the rotary segments are in the orientation shown in FIG. 13B, the fluid conduit 316a in the first rotary valve segment 324a is no longer aligned with the connector conduit in the first connector 316a but, instead, is now aligned with the connector conduit in the second connector 316b. Similarly, the second fluid conduit 316b in the second rotary valve segment 324b is no longer aligned with the connector conduit in the second connector 316b but, instead, is now aligned with the connector conduit in the third connector 316c. The inner opening in the first connector conduit is aseptically sealed. The first connector 316a is now aseptically sealed off from the other rotary valve segments 322a, 322b by the third rotary segment 322c. Thus, first connector housing 312a and the rotary valve segment 322c can be safely removed.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The particular implementations shown and described herein are illustrative examples of the invention and are not intended to otherwise limit the scope of the invention in any way. The use of any and all examples, or exemplary language (e.g., "such as") provided herein, is intended merely to better illuminate the invention and does not pose a limitation on the scope of the invention unless otherwise claimed. Numerous modifications and adaptations will be readily apparent to those skilled in this art without departing from the spirit and scope of the invention.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it were individually recited herein.

Terms such as "about" or "approximately", unless otherwise defined or restricted in the specification, should be understood to define a variance of plus or minus 5%-10% to the numerical term referred to.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed. The various embodiments and elements can be interchanged or combined in any suitable manner as necessary.

The use of directions, such as forward, rearward, top and bottom, upper and lower are with reference to the embodiments shown in the drawings and, thus, should not be taken as restrictive. Reversing or flipping the embodiments in the drawings would, of course, result in consistent reversal or flipping of the terminology.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalent.

The invention claimed is:

1. A coupler for aseptically coupling and controlling fluid communication between at least two components, the coupler comprising:
   a first connector housing including two opposed side walls, two opposed end walls, a top section and an open bottom, the side walls, the end walls and the top section each having respective inner surfaces that, in combination, define an inner cavity, and wherein the inner surfaces of the top section and the side sections define, in combination, a concave surface that has a shape that defines a portion of a cylinder;
   a first connector formed on or attached to and extending from the top section, the first connector adapted to connect to a first component of the at least two components;
   a first connector conduit extending through the first connector and the top section of the first connector housing so as to define a fluid passageway from an outer opening at an upper end of the first connector to an inner opening on the inner surface of the top section of the first connector housing;
   a rotary valve located within the inner cavity of the first connector housing and having a longitudinal axis, the rotary valve including at least two rotary valve segments, each rotary valve segment includes a valve segment outer surface and a valve segment inner surface, the valve segment outer surface having a curved surface that defines a portion of cylinder, and the valve segment inner surface having at least one inner planar surface, wherein the valve segment inner surface of one of the rotary valve segments is configured to contact the valve inner surface of an adjacent rotary valve segment, and wherein the curved outer surfaces of the rotary valve segments, in combination, define a cylindrical surface, and wherein the rotary valve segments are configured to rotate about the longitudinal axis within the cavity and against the concave inner surface of the first connector housing;
   wherein at least one of the at least two rotary valve segments includes a fluid conduit extending through the at least one rotary valve segment from a first opening to a second opening, the first opening being positioned so that:
      in a first rotational position of the at least one rotary valve segment relative to the first connector housing corresponding to the open state, the first opening aligns with the inner opening of the first connector conduit in the connector housing and the second opening of the fluid conduit simultaneously aligns with an inner opening on a second connector conduit so as to provide a fluid path from the outer opening of the first connector conduit and into the second connector conduit, and
      in a second rotational position of the at least one rotary valve segment relative to the first connector housing corresponding to the closed state, the first opening does not align with the inner opening of the first connector conduit in the connector housing, the second opening of the fluid conduit does not align with the inner opening on the second connector conduit, and the valve segment outer surface of one of the at least two rotary valve segments blocks the inner opening of the first connector housing and the valve segment outer surface of the other of the at least two rotary valve segments blocks the inner opening of the second connector housing conduit such that no fluid path is provided from the first connector conduit to the second connector conduit through either of the at least two rotary valve segments.

2. The aseptic coupler of claim 1, wherein the coupler includes a second connector housing adjacent to the first connect housing, the second connector housing have a second connector extending outward from a surface on the second connector housing, and wherein the second connector conduit extends through the second connector housing and the second connector, the second connector adapted to connect to a second component of the at least two components to thereby provide a fluid flow path between the first component and the second component.

3. The aseptic coupler of claim 2, wherein the second connector housing is a cap for a container and wherein the second component is the container configured to store a fluid.

4. The aseptic coupler of claim 2, wherein the second connector housing is a manifold, the manifold configured to receive multiple first connector housings.

5. The aseptic coupler of claim 2, wherein the second connector is a cap with threads that engage with a neck of a container.

6. The aseptic coupler of claim 2, wherein the second connector housing includes two opposed side walls, two opposed end walls, a top section and an open bottom, the side walls, the end walls and the top section each having respective inner surfaces that, in combination, define an inner cavity, and wherein the inner surfaces of the top section and the side sections define, in combination, a concave surface that has a shape that defines a portion of a cylinder; and wherein when the first and second connector housings are adjacent to one another the combination of the concave surfaces of the first and second connector housings form a substantially cylindrical shape.

7. The aseptic coupler of claim 1, wherein when the coupler is in the closed state, the first connector housing can be aseptically separated from a second connector housing so that the inner openings of the first and second connector conduits are not exposed to an ambient environment.

8. The aseptic coupler of claim 1, wherein when the coupler is in the closed state, at least one rotary valve segment is attached to the first connector housing such that the rotary valve segment cannot be readily removed from the first connector housing except by rotating the rotary valve segment relative to the first connector housing.

9. The aseptic coupler of claim 1, wherein each end wall of the first connector housing includes a protrusion extending into the cavity at a location radially inward from the side wall, each protrusion configured to mate with a corresponding recess formed in a longitudinal end of the corresponding rotary valve segment.

10. The aseptic coupler of claim 1, wherein there are three rotary valve segments, and further comprising a second connector and a third connector, each of the second connector and the third connector adapted to connect to one of the at least two components, and wherein two of the rotary valve segments include fluid conduits and the third rotary valve segment does not include any fluid conduit.

11. The aseptic coupler of claim 1, wherein the coupler includes at least three connector housings and the rotary valve includes at least three rotary valve segments.

12. The aseptic coupler of claim 1, further comprising a second connector and wherein the first and second connectors extend from the top of the first connector housing.

13. The aseptic coupler of claim 12, wherein the first and second connectors are hose barb connectors, each configured to connect with a separate hose that is coupled to an associated component of the at least two components.

14. The aseptic coupler of claim 1, wherein the coupler includes two rotary valve segments, wherein the valve segment outer surface of each rotary valve segment defines a semicylindrical surface, and the valve segment inner surface of each rotary valve segment is a planar surface.

15. The aseptic coupler of claim 14, wherein the coupler includes a second connector housing adjacent to the first connect housing, the second connector housing has a second connector extending outward from a surface on the second connector housing, and wherein the second connector conduit extends through the second connector housing and the second connector, the second connector adapted to connect to a second component of the at least two components to thereby provide a fluid flow path between the first component and the second component.

16. The aseptic coupler of claim 1, wherein each rotary valve segment includes a tab that is attached to or formed integral with a longitudinal end of the rotary valve segment.

17. The aseptic coupler of claim 16, wherein the tab includes a neck portion which is smaller in cross-section than the rotary valve segment, the neck portion seating within a first notch in one of the end walls, the first notch providing support for and permitting rotation of the neck portion relative to the first connector housing.

18. The aseptic coupler of claim 17, wherein each rotary valve segment includes a protrusion extending axially out of a longitudinal end of the rotary valve segment on an opposite side from the tab, the protrusion seating within a second notch in the other end wall of the connector housing, the second notch providing support for and permitting rotation of the protrusion relative to the first connector housing.

19. The aseptic coupler of claim 18, the coupler further comprising an assembly enclosure including two side walls that are spaced apart from one another a sufficient distance to receive the first and second connector housings, the assembly enclosure having top and bottom walls that are also spaced apart a distance to receive the first connector housing and the second connector housing therebetween, the top and bottom walls each including a notch to permit the first and second connectors to extend out of the assembly enclosure, the assembly enclosure having a back wall with a hole formed through it with notches on opposed sides that are sized and positioned so to permit the tabs on the at least two rotary valve segments to pass through and extend out of the enclosure when the closure is in its closed state, wherein the hole is sized to receive the neck portions of the tabs and permit the neck portions to rotate freely relative to the enclosure, wherein when the closure is in its closed state, the notches and hole permit the enclosure to be slid on and off the first and second connector housings, wherein when the closure is in its open position, the tabs are rotated relative to the notches so that the tabs prevent removal of the assembly enclosure.

\* \* \* \* \*